United States Patent
Miki et al.

(10) Patent No.: US 12,083,320 B2
(45) Date of Patent: Sep. 10, 2024

(54) INJECTOR AND METHOD OF INJECTING SOLUTION CONTAINING BIOMOLECULES INTO INJECTION TARGET USING THE SAME

(71) Applicant: DAICEL CORPORATION, Osaka (JP)

(72) Inventors: Katsuya Miki, Tokyo (JP); Shingo Atobe, Tokyo (JP); Hiroshi Miyazaki, Tokyo (JP); Ayano Suzuki, Tokyo (JP); Yuko Sakaguchi, Tokyo (JP)

(73) Assignee: Daicel Corporation, Osaka (JP)

( * ) Notice: Subject to any disclaimer, the term of this patent is extended or adjusted under 35 U.S.C. 154(b) by 1067 days.

(21) Appl. No.: 16/968,078

(22) PCT Filed: Feb. 8, 2019

(86) PCT No.: PCT/JP2019/004723
§ 371 (c)(1),
(2) Date: Aug. 6, 2020

(87) PCT Pub. No.: WO2019/156238
PCT Pub. Date: Aug. 15, 2019

(65) Prior Publication Data
US 2021/0023314 A1 Jan. 28, 2021

(30) Foreign Application Priority Data
Feb. 9, 2018 (JP) .................................. 2018-021909

(51) Int. Cl.
*A61M 5/30* (2006.01)
*A61M 5/20* (2006.01)
(Continued)

(52) U.S. Cl.
CPC ............ *A61M 5/30* (2013.01); *A61M 5/2046* (2013.01); *A61M 11/02* (2013.01); *A61M 11/001* (2014.02); *A61M 11/06* (2013.01)

(58) Field of Classification Search
CPC ...... A61M 11/02; A61M 5/30; A61M 11/001; A61M 11/06; A61M 5/2046
See application file for complete search history.

(56) References Cited

U.S. PATENT DOCUMENTS

| | | |
|---|---|---|
| 2005/0010168 A1 | 1/2005 | Kendall |
| 2009/0326446 A1 | 12/2009 | Alexandre |

(Continued)

FOREIGN PATENT DOCUMENTS

| | | |
|---|---|---|
| JP | 2002-511396 A | 4/2002 |
| JP | 2004-358234 A | 12/2004 |

(Continued)

OTHER PUBLICATIONS

International Search Report and Written Opinion mailed Mar. 26, 2019 in International Application No. PCT/JP2019/004723, in 15 pages.

(Continued)

*Primary Examiner* — Theodore J Stigell
(74) *Attorney, Agent, or Firm* — Knobbe Martens Olson & Bear LLP

(57) ABSTRACT

This application relates to an injector in which when a solution containing biomolecules is injected into an injection target, a proportion of biomolecules that function in the injection target with respect to the injected biomolecules is large. This application also relates to a method of injecting a solution containing biomolecules into an injection target using the injector. In one aspect, the injector injects the solution containing biomolecules into the injection target from an injector main body without performing injection (Continued)

through a given structure in a state where the given structure is inserted into the injection target. The injector may include an accommodation unit and a nozzle unit, wherein the injector satisfies a given condition.

5 Claims, 5 Drawing Sheets

(51) Int. Cl.
*A61M 11/02* (2006.01)
*A61M 11/00* (2006.01)
*A61M 11/06* (2006.01)

(56) References Cited

U.S. PATENT DOCUMENTS

| | | | | |
|---|---|---|---|---|
| 2018/0036486 A1* | 2/2018 | Yamamoto | ............ | A61M 5/315 |
| 2018/0168789 A1* | 6/2018 | Shiku | ................ | A61K 31/7088 |
| 2018/0188789 A1 | 6/2018 | Shiku et al. | | |
| 2018/0304019 A1 | 10/2018 | Oda et al. | | |
| 2018/0369484 A1* | 12/2018 | Nagamatsu | ......... | A61M 5/3129 |

FOREIGN PATENT DOCUMENTS

| | | | |
|---|---|---|---|
| JP | 2006-325700 A | | 12/2006 |
| JP | 2009-543634 | * | 12/2009 |
| JP | 2009-543634 A | | 12/2009 |
| JP | 2017-000667 A | | 1/2017 |
| WO | WO 99/52463 | | 10/1999 |
| WO | WO 2017/115868 A1 | | 7/2017 |

OTHER PUBLICATIONS

Extended European Search Report dated May 25, 2021 in EP 19751195.9, in 8 pages.

* cited by examiner

INJECTOR AND METHOD OF INJECTING SOLUTION CONTAINING BIOMOLECULES INTO INJECTION TARGET USING THE SAME

The present application is a U.S. national phase application under 35 U.S.C. § 371 of International Application No. PCT/JP2019/004723, filed on Feb. 8, 2019, which claims the benefit of Japanese Patent Application No. 2018-021909 filed on Feb. 9, 2018, in the Japanese Patent Office, the entire disclosure of each of which is incorporated herein by reference.

TECHNICAL FIELD

The present invention relates to an injector and a method of injecting a solution containing biomolecules into an injection target using the same.

BACKGROUND ART

Regarding injectors for injecting a drug solution into a living body or the like, there are catheters including an injection needle and a drive source for transporting a drug solution into an injection target in addition to a needle syringe that performs injection through an injection needle and a needleless syringe that performs injection without using an injection needle.

Among these, a needleless syringe may be configured to inject an injection component by applying a pressure to an accommodation chamber in which an injection solution is accommodated using a pressurized gas, a spring, or an electromagnetic force. For example, a configuration in which a plurality of nozzle holes are formed inside a syringe main body and a piston that is driven during injection is arranged to correspond to each nozzle hole may be used (Patent Document 1). With such a configuration, an injection solution is sprayed simultaneously from a plurality of nozzle holes and uniform injection into a target is realized. Then, a plasmid containing a luciferase gene can be injected into rats and cells can be transferred with high efficiency.

In addition, there is a form in which a pressurized gas is used as an injection power source for an injection solution in a needleless syringe. For example, a pressurization form in which a high pressure is instantaneously applied in the initial stage of injection, and the applied pressure is then gradually reduced over 40 to 50 msec may be exemplified (Patent Document 2).

However, there are no reports focusing on conditions for injecting a solution containing biomolecules from an injector when a proportion of biomolecules that function in the injection target with respect to the injected biomolecules is required to be increased, when a solution containing biomolecules is injected into an injection target using an injector.

PRIOR ART DOCUMENTS

Patent Document

[Patent Document 1] Japanese Patent Application Publication No. 2004-358234

[Patent Document 2] U.S. Patent Application Publication No. 2005/0010168

SUMMARY OF THE INVENTION

Problems to be Solved by the Invention

The present invention has been made in view of such circumstances, and an object of the present invention is to provide an injector in which when a solution containing biomolecules is injected into an injection target, a proportion of biomolecules that function in the injection target with respect to the injected biomolecules is large, and a method of injecting a solution containing biomolecules into an injection target using the injector.

Means for Solving the Problems

The inventors conducted extensive studies and as a result, found that, in an injector which accommodates a solution containing biomolecules, by focusing on an injection pressure rate which is a change in the injection pressure per unit time of the solution containing biomolecules within a predetermined time from the injection start time of the solution containing biomolecules injected by the injector and an injection pressure of the solution containing biomolecules within a predetermined time from the injection start time of the solution containing biomolecules, the following injector can address the above problems, and thus completed the present invention. The present invention is as follows.

[1] An injector that injects a solution containing biomolecules into an injection target from an injector main body without performing injection through a given structure in a state where the given structure is inserted into the injection target, the injector comprising:
an accommodation unit for accommodating a solution containing biomolecules; and
a nozzle unit including an injection port through which the solution containing biomolecules flows and is injected into the injection target, the solution being pressurized,
wherein an injection pressure rate which is a change in an injection pressure of the solution containing biomolecules per unit time from an injection start time of the solution containing biomolecules to a time of 0.20 ms is $7.0 \times 10^3$ MPa/s or more, and an injection pressure of the solution containing biomolecules from the injection start time of the solution containing biomolecules to 4.0 ms is less than 25 MPa.

[2] The injector according to [1],
wherein the injection pressure rate which is a change in an injection pressure of the solution containing biomolecules per unit time from an injection start time of the solution containing biomolecules to a time of 0.20 ms is $2.3 \times 10^4$ MPa/s or more.

[3] The injector according to [1] or [2],
wherein, in a first falling area of the injection pressure of the solution containing biomolecules, a period of time from a descending start time of a first peak injection pressure of the solution containing biomolecules to a time at which the injection pressure reaches a bottom value immediately after the first peak injection pressure is 6.0 ms or less.

[4] A method of injecting a solution containing biomolecules into an injection target using the injector according to any one of [1] to [3].

Effect of the Invention

According to the present invention, it is possible to provide an injector in which when a solution containing biomolecules is injected into an injection target, a proportion of biomolecules that function in the injection target with respect to the injected biomolecules is large, and a method of injecting a solution containing biomolecules into an injection target using the injector.

MODE FOR CARRYING OUT THE INVENTION

Figure 1:
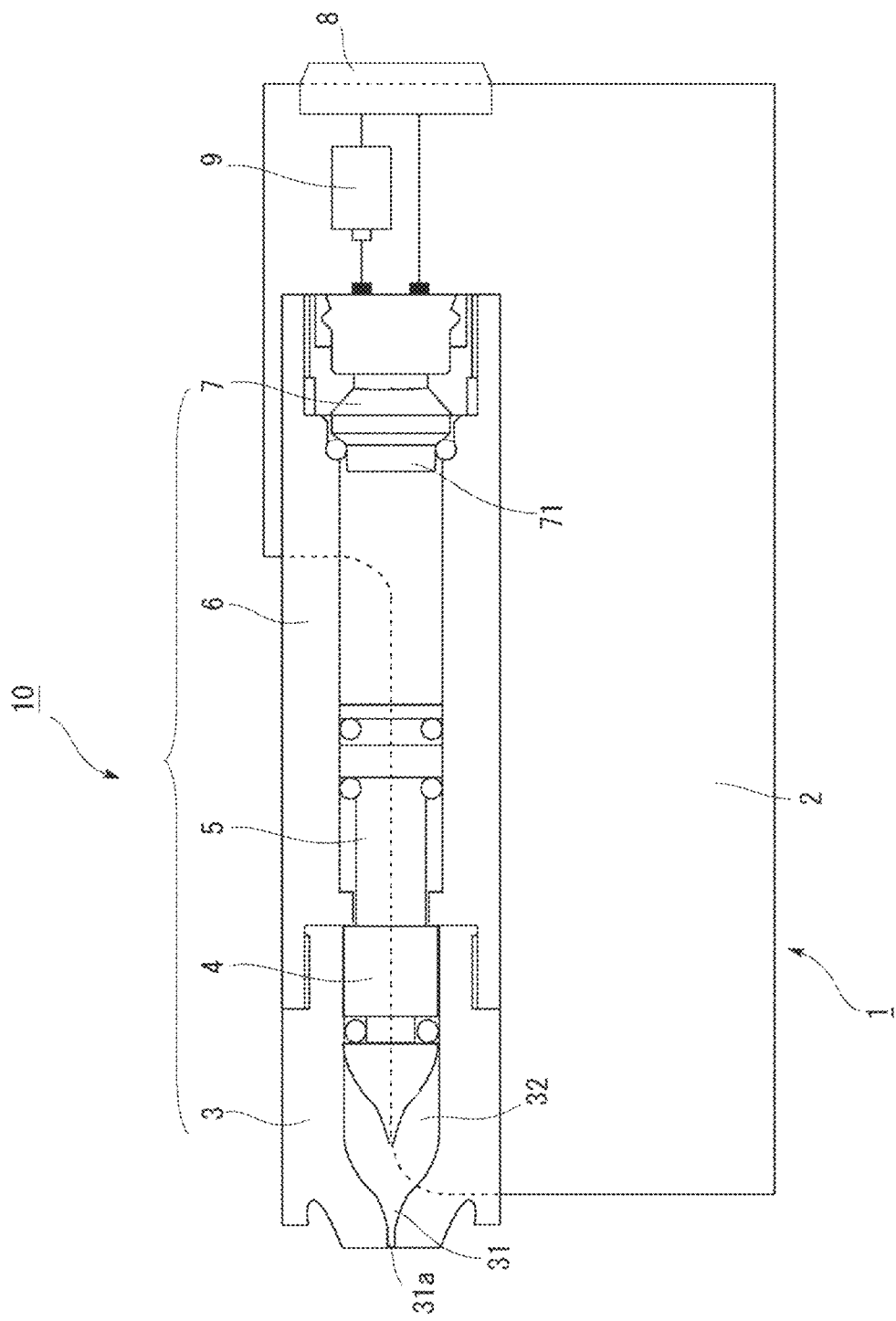
FIG. 1 is a diagram showing a schematic configuration of an injector according to one embodiment of a first aspect of the present invention.

The present invention includes an invention of an injector (first aspect) and an invention of a method of injecting a solution containing biomolecules to an injection target using the injector (second aspect).

First Aspect

The first aspect of the present invention is an injector that injects a solution containing biomolecules into an injection target from an injector main body without performing injection through a given structure in a state where the given structure is inserted into the injection target, the injector including: an accommodation unit for accommodating the solution containing biomolecules; and a nozzle unit including an injection port through which the solution containing biomolecules flows and is injected into the injection target, the solution being pressurized, wherein an injection pressure rate which is a change in an injection pressure of the solution containing biomolecules per unit time from an injection start time of the solution containing biomolecules to a time of 0.20 ms is $7.0 \times 10^3$ MPa/s or more, and an injection pressure of the solution containing biomolecules from the injection start time of the solution containing biomolecules to 4.0 ms is less than 25 MPa.

In the injector according to the first aspect of the present invention, if the injection pressure rate which is a change in an injection pressure of the solution containing biomolecules per unit time from the injection start time of the solution containing biomolecules to a time of 0.20 ms is $7.0 \times 10^3$ MPa/s or more, and the injection pressure of the solution containing biomolecules from the injection start time of the solution containing biomolecules to 4.0 ms is less than 25 MPa, when the solution containing biomolecules is injected into the injection target, it is possible to increase a proportion of biomolecules that function in the injection target with respect to the injected biomolecules.

Specifically, if the injection pressure rate of the solution containing biomolecules from the injection start time of the solution containing biomolecules to a time of 0.20 ms is $7.0\times10^3$ MPa/s or more, large deformation of the injection target is expected to be caused, and if the injection pressure of the solution containing biomolecules from the injection start time of the solution containing biomolecules to 4.0 ms is less than 25 MPa, excessive damage to the injection target is not expected. As a result, when the solution containing biomolecules is injected into the injection target, it is possible to increase a proportion of biomolecules that function in the injection target with respect to the injected biomolecules.

In this case, the injection pressure rate of the solution containing biomolecules from the injection start time of the solution containing biomolecules to a time of 0.20 ms is preferably $2.3\times10^4$ MPa/s or more, more preferably $3.4\times10^4$ MPa/s or more, and still more preferably $6.8\times10^4$ MPa/s or more. In addition, the upper limit is not particularly limited, and is, for example, $7.5\times10^4$ MPa/s or less.

In addition, the injection pressure of the solution containing biomolecules from the injection start time of the solution containing biomolecules to 4.0 ms is preferably 20 MPa or less, and is generally higher than 0 MPa, and is expected to be an output sufficient for delivering the solution containing biomolecules to the injection target, and thus it is preferably 1.5 MPa or more, more preferably 5.0 MPa or more, still more preferably 7.0 MPa or more, and yet more preferably 15 MPa or more.

In addition, if, in a first falling area of the injection pressure of the solution containing biomolecules, a period of time from a descending start time of a first peak injection pressure of the solution containing biomolecules to a time at which the injection pressure reaches a bottom value immediately after the first peak injection pressure is generally larger than 0 ms, and generally 6.0 ms or less, when the solution containing biomolecules is injected into the injection target, it is possible to increase a proportion of biomolecules that function in the injection target with respect to the injected biomolecules.

Here, the first peak injection pressure refers to an injection pressure at the earliest time among times at which the injection pressure of the solution containing biomolecules reaches a peak after injection of the solution containing biomolecules starts. In addition, the first falling area of the injection pressure of the solution containing biomolecules refers to an area in which the injection pressure of the solution containing biomolecules falls from the first peak injection pressure and the injection pressure falls to the bottom value immediately after the first peak injection pressure.

Specifically, if the period of time is 6.0 ms or less, the solution containing a sufficient amount of biomolecules is expected to have been delivered without excessively penetrating through the injection target due to a sudden liquid flow, and as a result, when the solution containing biomolecules is injected into the injection target, it is possible to increase a proportion of biomolecules that function in the injection target with respect to the injected biomolecules.

In this case, the period of time is preferably 4.1 ms or less, more preferably 1.0 ms or less, still more preferably 0.95 ms or less, yet more preferably 0.80 ms or less, and particularly preferably 0.40 ms or less. In addition, the period of time is generally greater than 0, and is preferably 0.30 ms or more.

In the first aspect of the present invention, the biomolecules to be injected into the injection target are not particularly limited as long as they function in the injection target when injected into the injection target. In addition, the biomolecules may be a natural product or artificially synthesized product. Examples thereof include nucleic acids or derivatives thereof; nucleosides, nucleotides or derivatives thereof; amino acids, peptides, proteins or derivatives thereof; lipids or derivatives thereof; metal ions; low-molecular-weight compounds or derivatives thereof; antibiotics; and vitamins or derivatives thereof. The nucleic acid may be DNA or RNA, and may include a gene. In examples to be described below, a free plasmid DNA containing a luciferase gene is used as a biomolecule, and the luciferase gene is used as a reporter gene.

The form of the biomolecules to be injected into the injection target and a solvent therefor are not particularly limited as long as biomolecules are stably present and there is no adverse effect such as destruction of the injection target to be injected, and may be a free form, a form in which biomolecules are fixed to carriers such as nanoparticles, a modified form.

When DNA contains a gene, a design form in which the gene is contained in an expression cassette or expression vector may be exemplified. In addition, for example, the gene may be provided under control of a promoter suitable for the type of the injection target into which the DNA is injected and the injection site. That is, in any of the forms, a known genetic engineering technique can be used. In examples to be described below, regarding the expression vector, a pGL3 control vector (commercially available from Promega Corporation) which is a mammalian expression vector is used. The plasmid vector is known, and is available for those skilled in the art. Subcloning of the expression vector and the recombinant vector can be performed according to a known method.

(Function of Biomolecules)

As an example in which a proportion of biomolecules that function in the injection target with respect to the biomolecules injected into the injection target is large, a case in which, when DNA as a biomolecule contains a gene, a high expression level of the gene with respect to the amount of DNA injected into the injection target may be exemplified. As a confirmation method, for example, as shown in examples to be described below, after a DNA solution is injected into the injection target, tissues are collected in a cylindrical shape having a desired radius around an injection port for the DNA solution, a sample is prepared by a known biological method, and an expression level assay of the gene can be used for confirmation. An appropriate known method can be used depending on the type of the gene and the like. For example, when the gene is a luciferase gene, a case in which an amount of luminescence is assayed using luciferin as a substrate may be exemplified.

In the injector according to the first aspect of the present invention, "distal end side" refers to the side on which an injection port through which a solution containing biomolecules is injected from an injector is arranged, and "proximal end side" refers to the side opposite to the distal end side in the injector, and these terms do not limit specific locations or positions.

The injector according to the first aspect of the present invention injects a solution containing biomolecules to the injection target from an injector main body without performing injection through a given structure in the state where the given structure is inserted into the injection target. The injector according to the first aspect of the present invention may have, for example, a given structure such as a catheter for guiding a solution containing biomolecules from an injector main body to an injection target, for example, when a distance from the injector main body to the injection target is large. Therefore, the injector according to the first aspect of the present invention may or may not have such a given structure. However, when the injector has such a given structure, a solution containing biomolecules is not injected into the injection target in the state where the given structure is inserted into the injection target.

In the injector according to the first aspect of the present invention, a driving unit for pressurizing a solution containing biomolecules is not particularly limited. The pressurization may be caused by, for example, a pressure generated when the pressure of the compressed gas is released, or a pressure generated by combustion of an explosive that is ignited by an ignition device. In addition, pressurization using an electromagnetic force, for example, pressurization using a linear electromagnetic actuator, may be used. Preferably, at least, a form in which a pressure generated by combustion of an explosive that is ignited by an ignition device is used, or any one of two other pressurization forms or a combination of them may be used.

When a form in which a pressure generated by combustion of an explosive that is ignited by an ignition device is used for pressurization is used, the explosive may be, for example, any explosive among an explosive containing zirconium and potassium perchlorate (ZPP), an explosive containing titanium hydride and potassium perchlorate (THPP), an explosive containing titanium and potassium perchlorate (TiPP), an explosive containing aluminum and potassium perchlorate (APP), an explosive containing aluminum and bismuth oxide (ABO), an explosive containing aluminum and molybdenum oxide (AMO), an explosive containing aluminum and copper oxide (ACO), and an explosive containing aluminum and iron oxide (AFO) or an explosive composed of a plurality of combinations of these. Regarding a feature of these explosives, if the combustion products are gases in a high temperature state, since they do not contain gas components at room temperature, the combustion products after ignition immediately condense.

In addition, when the generated energy of a gas generating agent is used as injection energy, various gas generating agents used in a single base smokeless explosive, a gas generator for an airbag, and a gas generator for a seat belt pretensioner can be used as the gas generating agent.

In the injector according to the first aspect of the present invention, the solution containing biomolecules is not accommodated in a filling chamber from the beginning, and the solution containing biomolecules is accommodated in the filling chamber by sucking through a nozzle having an injection port. In this manner, when a configuration in which a filling operation in the filling chamber is required is used, it is possible to inject any required solution containing biomolecules into the injection target. Therefore, in the injector according to the first aspect of the present invention, a syringe part is removable.

Hereinafter, regarding an example of an injector according to one embodiment of the first aspect of the present invention, a syringe 1 (needleless syringe) will be described with reference to the drawings. Here, the configuration of the following embodiment is an example, and the first aspect of the present invention is not limited to the configuration of the embodiment. Here, the terms "distal end side" and "proximal end side" are used as terms that represent the relative positional relationships in the syringe 1 in the longitudinal direction. The "distal end side" represents a position near the tip of the syringe 1 to be described below, that is, near an injection port 31a, and the "proximal end side" represents a side on the side opposite to the "distal end side" of the syringe 1 in the longitudinal direction, that is, a side on the side of a driving unit 7. In addition, this example is an example in which combustion energy of an explosive that is ignited by an ignition device is used as injection energy and a DNA solution is used as a solution containing biomolecules, but the first aspect of the present invention is not limited thereto.

(Configuration of Syringe 1)

FIG. 1 is a diagram showing a schematic configuration of the syringe 1 and is a cross-sectional view of the syringe 1 in the longitudinal direction. The syringe 1 has a configuration in which a syringe assembly 10 in which a sub-assembly including a syringe part 3 and a plunger 4 and a sub-assembly including a syringe main body 6, a piston 5, and the driving unit 7 are integrally assembled is mounted in a housing (syringe housing) 2.

As described above, the syringe assembly 10 is configured to be detachable from the housing 2. A filling chamber 32 formed between the syringe part 3 and the plunger 4 included in the syringe assembly 10 is filled with a DNA solution, and the syringe assembly 10 is a unit that is discarded whenever the DNA solution is injected. On the other hand, on the side of the housing 2, a battery 9 that supplies power to an igniter 71 included in the driving unit 7 of the syringe assembly 10 is included. When a user performs an operation of pressing a button 8 provided in the housing 2, supply of power from the battery 9 is performed between an electrode on the side of the housing 2 and an electrode on the side of the driving unit 7 of the syringe assembly 10 via a wiring. Here, the shape and position of both electrodes are designed so that the electrode on the side of the housing 2 and the electrode on the side of the driving unit 7 of the syringe assembly 10 are automatically brought in contact when the syringe assembly 10 is mounted in the housing 2. In addition, the housing 2 is a unit that can be repeatedly used as long as power that can be supplied to the driving unit 7 remains in the battery 9. Here, in the housing 2, when the battery 9 has no power, only the battery 9 may be replaced, and the housing 2 may be continuously used.

In addition, in the syringe main body 6 shown in FIG. 1, no particular additional explosive component is provided, but in order to adjust transition of the pressure applied to the injection solution via the piston 5, a gas generating agent that generates a gas and the like by combustion of a combustion product generated by explosive combustion in the igniter 71 can be provided in the igniter 71 or in a through-hole of the syringe main body 6. A configuration in which a gas generating agent is provided in the igniter 71 is an already known technique as disclosed in WO 01-031282, Japanese Patent Application Publication No. 2003-25950, and the like. In addition, regarding an example of a gas generating agent, a single base smokeless explosive including 98 mass % of nitrocellulose, 0.8 mass % of diphenylamine, and 1.2 mass % of potassium sulfate may be exemplified. In addition, various gas generating agents used in a gas generator for an airbag and a gas generator for a seat belt pretensioner can be used. When the dimensions, the size, the shape, and particularly, the surface shape of the gas generating agent when provided in the through-hole is adjusted, it is possible to change a combustion completion time of the gas generating agent, and thus the transition of the pressure applied to the DNA solution can be a desired transition, that is, a transition in which the DNA solution can be appropriately injected into the injection target. In the first aspect of the present invention, the driving unit 7 includes a gas generating agent and the like used as necessary.

(Injection Target)

The injection target in the first aspect of the present invention has no limitation, and may be, for example, any of cells, cell sheets, tissues, organs (body organs), organ systems, and individuals (living bodies). In addition, regarding an upper hierarchy in a part of an injection target, a lower hierarchy contained in the part may be the target. That is, for example, when tissues are an injection target, cells contained in the tissues may be the injection target, an intercellular matrix contained in the tissues may be the injection target, or both may be the injection target.

Examples of a preferable injection target include injection targets derived from mammals. The target is more preferably the skin of a mammalian individual (living body), and still more preferably one or more tissues selected from the group consisting of intradermal, subcutaneous and cutaneous muscles in the skin. In this case, a method in which a solution containing biomolecules is injected from an injector into a skin surface of a mammalian individual (living body), and injected from the skin surface into one or more tissues selected from the group consisting of intradermal, subcutaneous and cutaneous muscles in the skin can be used.

In addition, a system in which a solution containing biomolecules is injected from an injector into an injection target may be any of an in vitro system, an in vivo system, and an ex vivo system.

In addition, the mammal is not particularly limited, and examples thereof include humans, mice, rats, guinea pigs, hamsters, cows, goats, sheep, swine, monkeys, dogs, and cats. In addition, depending on the injection target, a form in which humans are excluded from mammals may be exemplified.

Second Aspect

The second aspect of the present invention is a method of injecting a solution containing biomolecules into an injection target using the injector of the first aspect.

The description of the first aspect of the present invention described above applies to the injector, the injection target, and the solution containing biomolecules in the second aspect of the present invention.

EXAMPLES

Hereinafter, the present invention will be described in more detail with reference to examples, but the present invention is not limited to the following examples without departing from the spirit and scope of the invention.

Evaluation of Injection Pressure of Injector

Example 1-1

An injector shown in FIG. 1 (nozzle diameter: diameter of 0.1 mm) was filled with 100 μL of water, and the injection pressure in the injector from when pressurization of water was performed by combustion of an ignition charge until after injection was evaluated. Regarding the explosive, 55 mg of an explosive containing zirconium and potassium perchlorate (ZPP) was used, and regarding the gas generating agent, 40 mg of a single base smokeless explosive (hereinafter referred to as "GG" in some cases) was used.

For measurement of the injection pressure, like the measurement method in Japanese Patent Application Publication No. 2005-21640, a method in which an injection force was distributed and applied to a diaphragm of a load cell arranged downstream from a nozzle, an output from the load cell was collected in a data collection display device via a detection amplifier, and displayed and stored as an injection force (N) for each time was used for measurement, and the injection pressure was calculated by dividing the injection force (N) by an area of a nozzle port.

Example 1-2

This example was the same as Example 1-1 except that 35 mg of ZPP was used.

Example 1-3

This example was the same as Example 1-1 except that 15 mg of ZPP was used.

Example 1-4

This example was the same as Example 1-1 except that 25 mg of ZPP was used.

Figure 2:
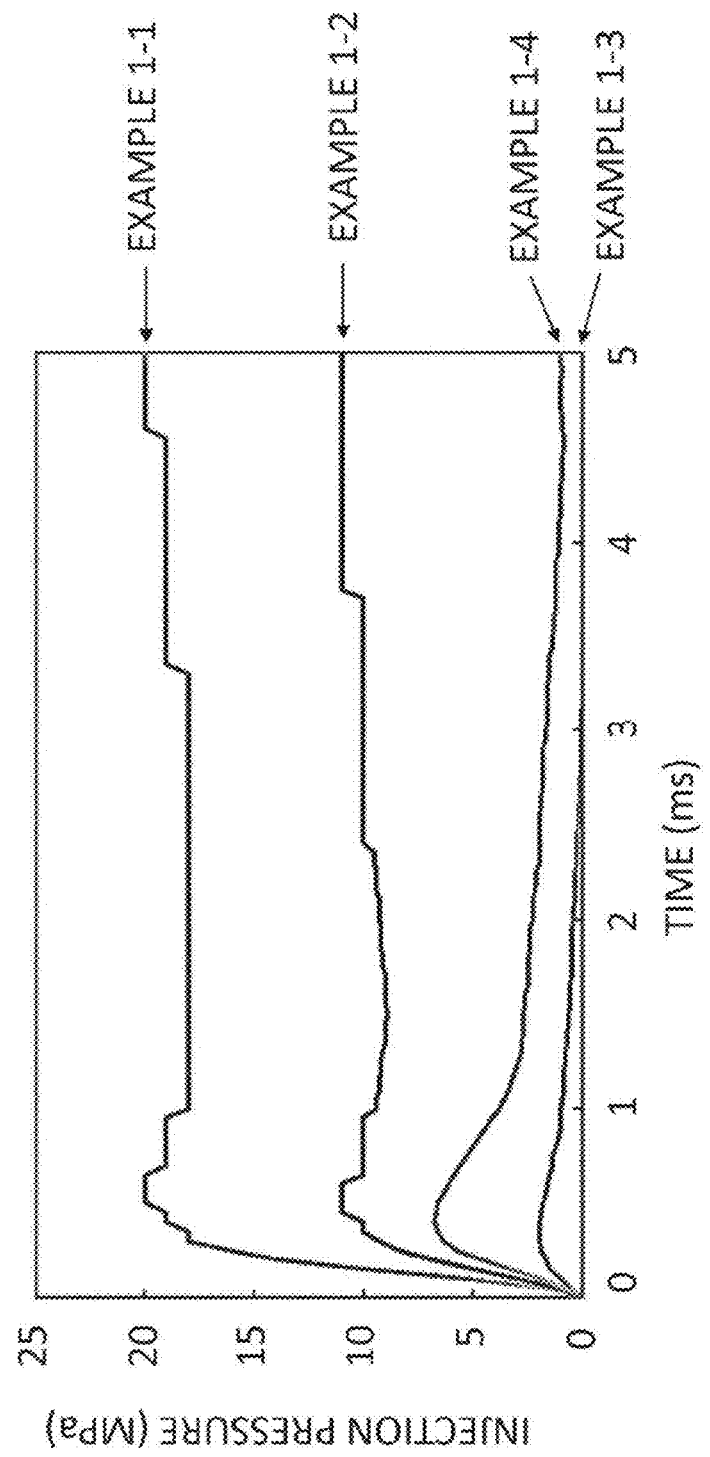
FIG. 2 is a graph showing an injection pressure of filled water according to one embodiment of the first aspect of the present invention over time.
Figure 3:
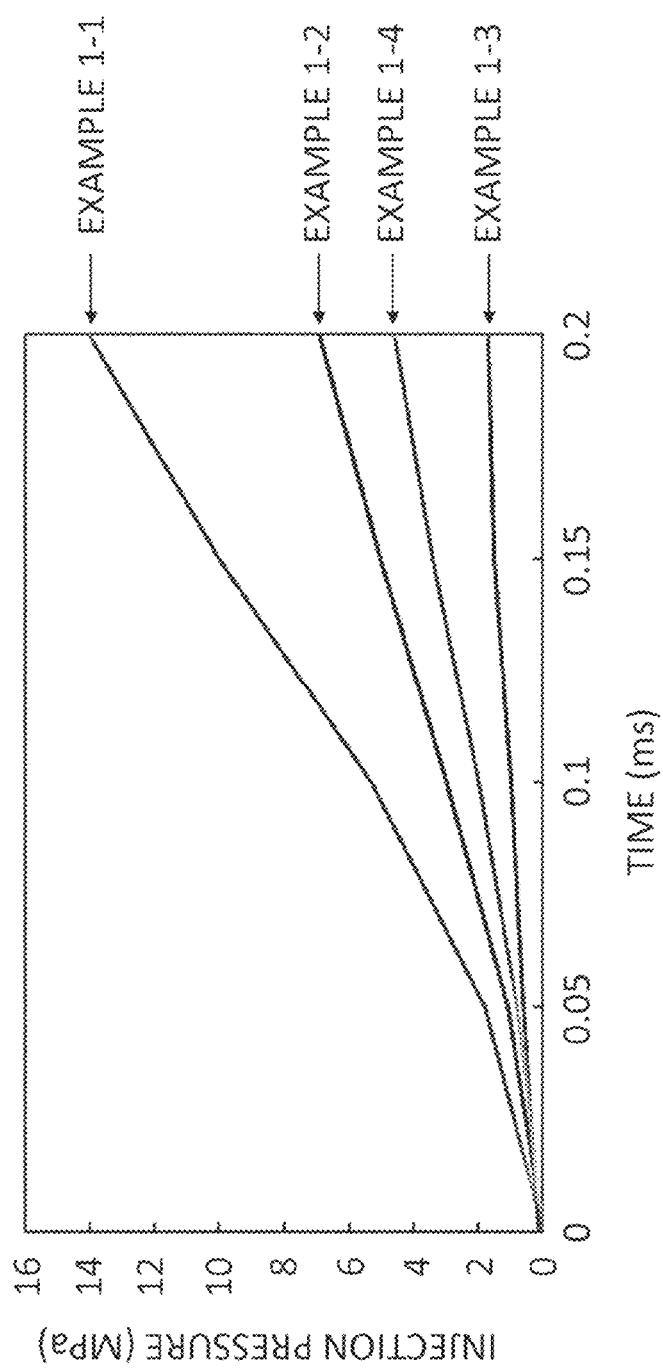
FIG. 3 is a graph showing an injection pressure of filled water according to one embodiment of the first aspect of the present invention over time.

FIG. 2 is a graph showing an injection pressure of water over time in examples. In addition, FIG. 3 is an enlarged graph for the initial 0.20 ms in FIG. 2. In addition, Table 1 shows parameters.

a dry ice atmosphere for about 15 minutes and frozen. It was confirmed that the tube had frozen and it was left to thaw at room temperature for about 20 minutes. This freezing and thawing were repeated three times in total to promote cell destruction. Then, the sample was centrifuged (at a temperature of 4° C., a rotation speed of 2,000 rpm, for a time of 5 min) to obtain a supernatant.

The luciferase assay was performed using Lumitester C100 (commercially available from Kikkoman Biochemifa Company). First, the Luciferase Assay Substrate of the Luciferase assay system was returned to room temperature and opened, and 10 mL of the Luciferase Assay Buffer returned to room temperature was added thereto. The mixture was lightly shaken to avoid foaming and the dissolved state was confirmed. 100 μL of the mixture was added to a Lumitube, and 20 μL of a serum sample to be measured was added. The sample was put into a Lumitester measurement chamber within about 20 seconds and measured to obtain a luminous intensity. The luminous intensity correlated with the expression level of the luciferase gene.

Example 2-2

This example was the same as Example 2-1 except that the injector used in Example 1-2 was used.

TABLE 1

| | ZPP (mg) | GG (mg) | Injection pressure rate (MPa/s) (*1) | Maximum injection pressure (MPa) (*2) | Descending start time A (ms) of first peak injection pressure | First peak injection pressure (MPa) | Time B at which injection pressure reaches bottom value immediately after first peak injection pressure (ms) | Left bottom value (MPa) | Time A − B (ms) |
|---|---|---|---|---|---|---|---|---|---|
| Example 1-1 | 55 | 40 | 6.8E+04 | 20 | 0.65 | 20 | 1.00 | 18 | 0.35 |
| Example 1-2 | 35 | 40 | 3.4E+04 | 11 | 0.60 | 11 | 1.50 | 8.9 | 0.90 |
| Example 1-3 | 15 | 40 | 8.0E+03 | 2.0 | 0.40 | 2.0 | 1.15 | 0.84 | 0.75 |
| Example 1-4 | 25 | 40 | 2.3E+04 | 6.8 | 0.40 | 6.8 | 4.50 | 0.88 | 4.1 |

(*1). Injection pressure rate which is a change in an injection pressure of a solution containing biomolecules per unit time from an injection start time of the solution containing biomolecules to a time of 0.20 ms.
(*2). Maximum injection pressure of the solution containing biomolecules between the injection start time of the solution containing biomolecules and 4.0 ms.

Evaluation of Gene Expression Using Rats

Example 2-1

The injector used in Example 1-1 was filled with 30 μL of a solution (solvent: endotoxin-free TE buffer, final concentration: 1.0 mg/mL) containing a plasmid pGL3-control vector containing a luciferase gene (commercially available from Promega Corporation), and the solution was injected into the skin of the lumbar back of a female SD rat (10-week old).

1.5 mL of "Cell Culture Lysisx5" of Luciferase assay system (commercially available from Promega Corporation) diluted fivefold was put into a 2 mL micro tube to prepare a dissolution liquid, and a tissue from intradermal muscles to skin muscles (that is, intradermal, subcutaneous and cutaneous muscles) around the injection port was cut into a size of about 1 square cm and added to the dissolution liquid. The tissue in the dissolution liquid was finely cut into fine particles of 2 square mm or less using dissection scissors (about 2 minutes, the scissors were moved about 100 times) and stirred with a vortex mixer or an ultrasonic washer for 10 seconds. Next, the micro tube was left at −80° C. or under Example 2-3

This example was the same as Example 2-1 except that the injector used in Example 1-3 was used.

Example 2-4

This example was the same as Example 2-1 except that the injector used in Example 1-4 was used.

Figure 4:
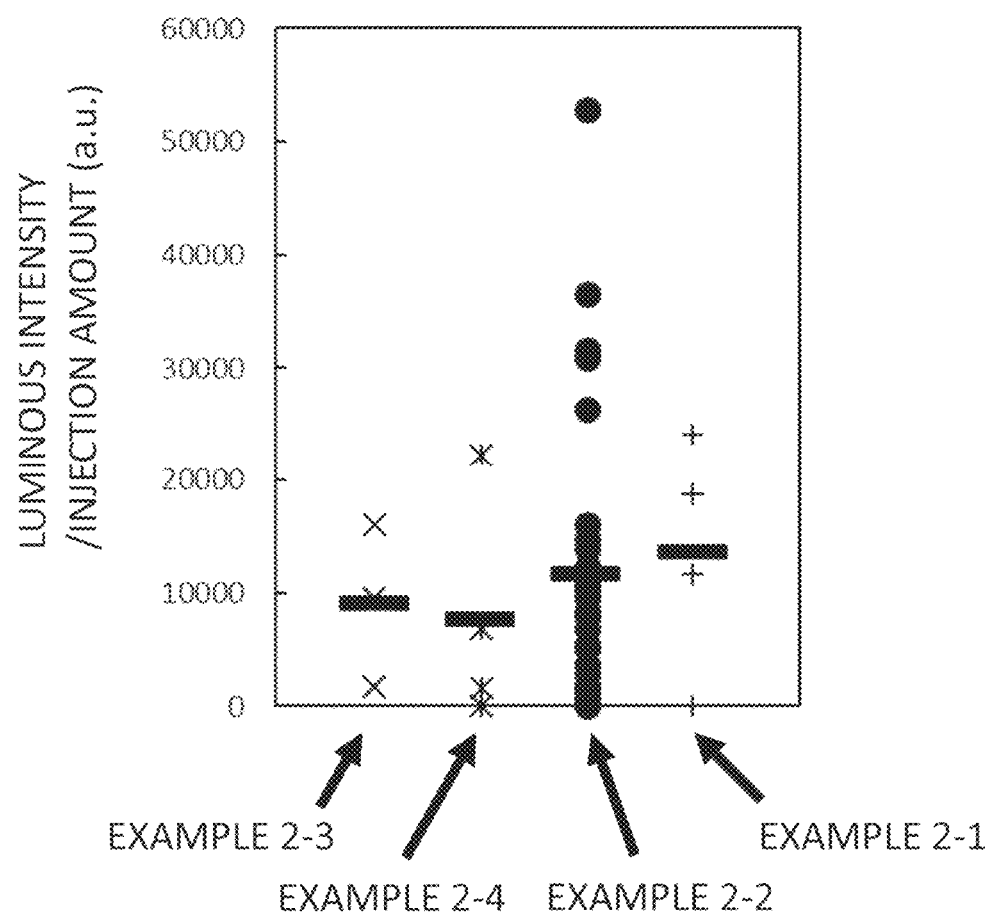
FIG. 4 is a graph showing a value obtained by dividing an expression level (luminous intensity) of a gene after a plasmid DNA solution containing the gene is injected into rats by an injection amount of the plasmid DNA solution according to one embodiment of a second aspect of the present invention.

FIG. 4 is a graph showing a value obtained by dividing an expression level (luminous intensity) of a luciferase gene by an injection amount of plasmid DNA in examples. The horizontal line in the graph represents the average value.

Evaluation of Gene Expression Using Swine

Example 3-1

This example was the same as Example 2-1 except that the injector used in Example 1-1 was filled with 100 μL of a solution (solvent: endotoxin-free TE buffer, final concentration: 1 mg/mL) containing a plasmid pGL3-control vector containing a luciferase gene (commercially available from Promega Corporation), and the solution was injected into the skin of the abdomen of a female edible swine (3-month old, body weight about 65 kg), and after culturing for 24 hours, an intradermal tissue was used as a luciferase assay sample.

Figure 5:
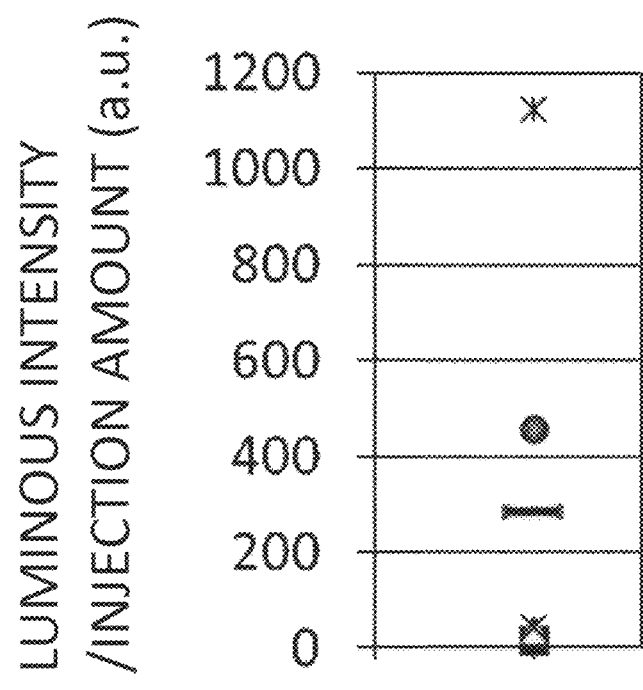
FIG. 5 is a graph showing a value obtained by dividing an expression level (luminous intensity) of a gene after a plasmid DNA solution containing the gene is injected into swine by an injection amount of the plasmid DNA solution according to one embodiment of a second aspect of the present invention.

FIG. 5 is a graph showing a value obtained by dividing the expression level (luminous intensity) in the luciferase gene by a plasmid DNA injection amount in Example 3-1. The horizontal line in the graph represents the average value.

DESCRIPTION OF REFERENCE NUMERALS

1: Syringe, 2: Housing, 3: Syringe part, 4: Plunger, 5: Piston, 6: Syringe main body, 7: Driving unit, 8: Button, 9: Battery, 10: Syringe assembly, 31: Nozzle unit, 31a: Injection port, 32: Filling chamber, 71: Igniter

The invention claimed is:

1. A needleless injector that injects a solution containing biomolecules into an injection target the injector comprising:
   a filling chamber configured to accommodate a solution containing biomolecules;
   a drive comprising a gas generating agent configured to generate a gas;
   a nozzle including an injection port configured to inject the solution containing biomolecules into the injection target, wherein the injection target comprises biomolecules therein configured to function in the injection target; and
   a piston configured to pressurize the solution containing biomolecules based on the generated gas, prior to the solution containing biomolecules being injected into the injection target, at an injection pressure rate of $6.8 \times 10^4$ MPa/s or more and at an injection pressure of being less than 25 MPa such that a proportion of the biomolecules functioning in the injection target with respect to the injected biomolecules is higher after the solution containing biomolecules is injected into the injection target than before the solution containing biomolecules is injected into the injection target,
   wherein the injection pressure rate is defined as a change in an injection pressure of the solution containing biomolecules per unit time from an injection start time of the solution containing biomolecules to a time of 0.20 ms, and wherein the injection pressure is defined as an injection pressure of the solution containing biomolecules from the injection start time of the solution containing biomolecules to 4.0 ms.

2. The injector according to claim 1, wherein, in a first falling area of the injection pressure of the solution containing biomolecules, a period of time from a descending start time of a first peak injection pressure of the solution containing biomolecules to a time at which the injection pressure reaches a bottom value immediately after the first peak injection pressure is 6.0 ms or less.

3. The injector according to claim 1, wherein the injection pressure rate is greater than $6.8 \times 10^4$ MPa/s and not greater than $7.5 \times 10^4$ MPa/s.

4. The injector according to claim 1, wherein the piston is configured to pressurize the solution containing biomolecules at the injection pressure rate and at the injection pressure based on at least one of a dimension, a size, a shape, or a surface shape of the gas generating agent.

5. A method of injecting a solution containing biomolecules into an injection target using the injector according to claim 1.

* * * * *